(12) United States Patent
Pinedjian et al.

(10) Patent No.: US 7,740,619 B2
(45) Date of Patent: Jun. 22, 2010

(54) SPRING DRIVEN OPHTHALMIC INJECTION DEVICE WITH SAFETY ACTUATOR LOCKOUT FEATURE

(75) Inventors: Raffi Pinedjian, Fountain Valley, CA (US); Robert J. Sanchez, Jr., Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 172 days.

(21) Appl. No.: 12/025,868

(22) Filed: Feb. 5, 2008

(65) Prior Publication Data

US 2009/0036868 A1 Feb. 5, 2009

Related U.S. Application Data

(63) Continuation-in-part of application No. 11/832,301, filed on Aug. 1, 2007, and a continuation-in-part of application No. 11/832,333, filed on Aug. 1, 2007, and a continuation-in-part of application No. 11/832,243, filed on Aug. 1, 2007, and a continuation-in-part of application No. 11/832,364, filed on Aug. 1, 2007.

(51) Int. Cl.
*A61M 5/315* (2006.01)
(52) U.S. Cl. ..................................... 604/220
(58) Field of Classification Search ............... 604/187, 604/181, 207, 220
See application file for complete search history.

(56) References Cited

U.S. PATENT DOCUMENTS 1,252,614 A    1/1918  Pieper et al.
3,089,815 A    5/1963  Lieb et al.
3,608,549 A    9/1971  Merrill (Continued)

FOREIGN PATENT DOCUMENTS

EP    0348146 A1    6/1989

(Continued)

OTHER PUBLICATIONS

"Ultra (TM) 2800 positive displacement;" 2004; EFD, Inc. Brochure XP 1104 vol. 11.10; 2 pages.

(Continued)

*Primary Examiner*—Kevin C Sirmons
*Assistant Examiner*—Deanna K Hall
(74) *Attorney, Agent, or Firm*—Kenneth D. Bassinger

(57) ABSTRACT

An ophthalmic injection device includes a dispensing chamber housing with an inner surface that partially defines a dispensing chamber for holding a substance, a plunger fluidly sealed to the interior surface of the dispensing chamber housing, and a needle fluidly coupled to the dispensing chamber. A temperature control device partially surrounds the dispensing chamber housing and alters a temperature of the substance. A piston is coupled to the plunger at one end and to a spring at the other end. The spring provides a force to drive the piston and the plunger. An actuator is coupled to the lockout bar with which a button is configured to interface. The actuator moves the lockout bar when the substance reaches a temperature, thereby allowing the button to be activated so that the spring provides the force to drive the plunger. An incorporated stop whose measurements may vary allow the expelled dosage to vary accordingly.

21 Claims, 5 Drawing Sheets

U.S. PATENT DOCUMENTS

| | | | |
|---|---|---|---|
| 3,892,537 | A | 7/1975 | Gulati et al. |
| 4,007,742 | A | 2/1977 | Banko |
| 4,030,499 | A | 6/1977 | Bucalo |
| 4,054,138 | A | 10/1977 | Bucalo |
| 4,122,850 | A | 10/1978 | Bucalo |
| 4,184,510 | A | 1/1980 | Murry et al. |
| 4,246,932 | A | 1/1981 | Raines |
| 4,265,618 | A | 5/1981 | Herskovitz et al. |
| 4,357,136 | A | 11/1982 | Herskovitz et al. |
| 4,392,827 | A | 7/1983 | Martin |
| 4,474,752 | A | 10/1984 | Haslam et al. |
| 4,484,915 | A | 11/1984 | Tartaglia |
| 4,582,488 | A | 4/1986 | Newman |
| 4,684,344 | A * | 8/1987 | Brockway et al. ............. 433/81 |
| 4,704,088 | A | 11/1987 | Newman |
| 4,713,446 | A | 12/1987 | DeVore et al. |
| 4,795,423 | A | 1/1989 | Osterholm |
| 4,830,855 | A | 5/1989 | Stewart |
| 4,992,045 | A | 2/1991 | Beisel |
| 5,066,276 | A | 11/1991 | Wang |
| 5,120,307 | A | 6/1992 | Wang |
| 5,328,481 | A | 7/1994 | Wang |
| 5,336,175 | A | 8/1994 | Mames |
| 5,360,413 | A | 11/1994 | Leason et al. |
| 5,370,630 | A | 12/1994 | Smidebush et al. |
| 5,476,511 | A | 12/1995 | Gwon et al. |
| 5,487,725 | A | 1/1996 | Peyman |
| 5,582,595 | A | 12/1996 | Haber et al. |
| 5,620,700 | A | 4/1997 | Berggren et al. |
| 5,743,886 | A | 4/1998 | Lynn et al. |
| 5,773,019 | A | 6/1998 | Ashton et al. |
| 5,783,205 | A | 7/1998 | Berggren et al. |
| 5,824,072 | A | 10/1998 | Wong |
| 5,860,949 | A | 1/1999 | Chen |
| 5,928,663 | A | 7/1999 | Peyman |
| 5,984,889 | A | 11/1999 | Christ et al. |
| 6,210,357 | B1 | 4/2001 | Morris |
| 6,270,343 | B1 | 8/2001 | Martin |
| 6,290,690 | B1 | 9/2001 | Huculak et al. |
| 6,364,865 | B1 | 4/2002 | Lavi et al. |
| 6,372,245 | B1 | 4/2002 | Bowman et al. |
| 6,413,245 | B1 | 7/2002 | Yaacobi et al. |
| 6,419,656 | B1 | 7/2002 | Vetter et al. |
| 6,436,143 | B1 | 8/2002 | Ross et al. |
| 6,488,659 | B1 | 12/2002 | Rosenman |
| 6,520,930 | B2 | 2/2003 | Critchlow et al. |
| 6,585,700 | B1 | 7/2003 | Trocki et al. |
| 6,595,979 | B1 | 7/2003 | Epstein et al. |
| 6,635,267 | B1 | 10/2003 | Miyoshi et al. |
| 6,645,179 | B1 | 11/2003 | Ishikawa et al. |
| 6,726,654 | B2 | 4/2004 | Rosenman |
| 6,940,209 | B2 | 9/2005 | Henderson |
| 6,991,457 | B2 | 1/2006 | Kazen et al. |
| 7,176,030 | B2 | 2/2007 | Faries, Jr. et al. |
| 2002/0055720 | A1 | 5/2002 | Hohlfelder et al. |
| 2003/0055380 | A1 | 3/2003 | Flaherty |
| 2003/0125665 | A1 | 7/2003 | Rosenman |
| 2004/0039253 | A1 | 2/2004 | Peyman et al. |
| 2004/0052761 | A1 | 3/2004 | Vernon et al. |
| 2004/0133155 | A1 | 7/2004 | Varner et al. |
| 2004/0176720 | A1 | 9/2004 | Kipfer |
| 2004/0210200 | A1 | 10/2004 | Gerondale et al. |
| 2004/0231667 | A1 | 11/2004 | Horton et al. |
| 2005/0065477 | A1 | 3/2005 | Jost |
| 2005/0177137 | A1* | 8/2005 | Kipfer ................... 604/890.1 |
| 2006/0047250 | A1* | 3/2006 | Hickingbotham et al. ... 604/187 |

FOREIGN PATENT DOCUMENTS

| | | |
|---|---|---|
| EP | 0398394 B1 | 11/1990 |
| GB | 1551767 | 5/1979 |
| WO | WO 82/03761 A1 | 11/1982 |
| WO | WO 87/00029 A1 | 1/1987 |
| WO | WO 96/03978 | 2/1996 |
| WO | WO 99/33853 | 7/1999 |
| WO | WO 01/10482 A1 | 2/2001 |
| WO | WO 2006/050008 A1 | 5/2006 |

OTHER PUBLICATIONS

"Parker: Your Resource for Motion and Fluid Control Components, Systems and Solutions—System Solutions for Life Sciences;" 2003; Aurora Instruments, LLC Brochure; 8 pages.

* cited by examiner

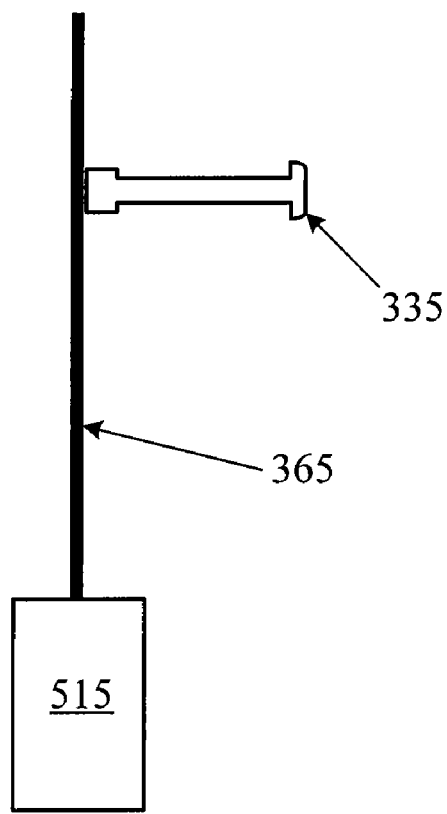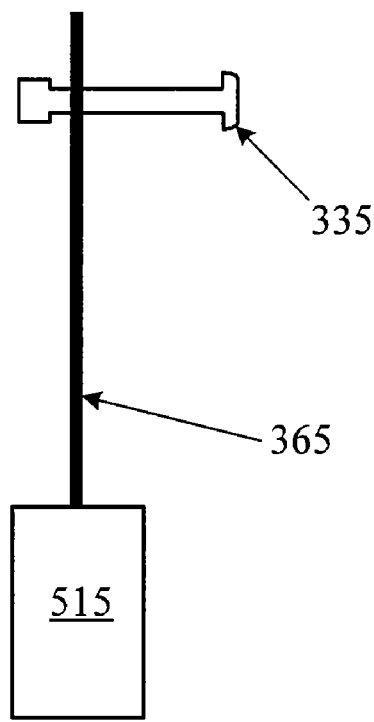
Fig. 4A                    Fig. 4B
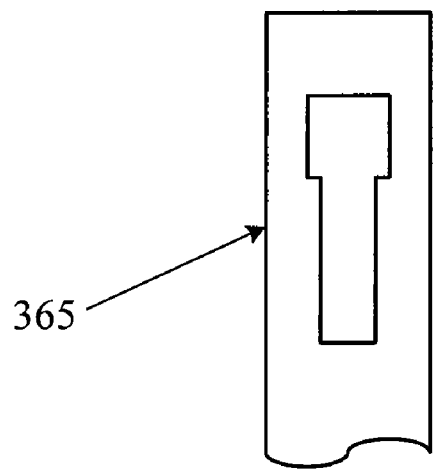
Fig. 5

SPRING DRIVEN OPHTHALMIC INJECTION DEVICE WITH SAFETY ACTUATOR LOCKOUT FEATURE

RELATED APPLICATIONS

This Application is a continuation-in-part of U.S. patent application Ser. No. 11/832,301 filed Aug. 1, 2007, U.S. patent application Ser. No. 11/832,333 filed Aug. 1, 2007, U.S. patent application Ser. No. 11/832,243 filed Aug. 1, 2007, U.S. patent application Ser. No. 11/832,364 filed Aug. 1, 2007.

BACKGROUND OF THE INVENTION

The present invention relates to a single-use medical device and more particularly to a two-piece ophthalmic drug delivery device with a disposable tip end containing a sintered ceramic chamber.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually performed using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to pierce the eye tissue with the needle, hold the syringe steady, and actuate the syringe plunger (with or without the help of a nurse) to inject the fluid into the eye. The volume injected is typically not controlled in an accurate manner because reading the vernier is subject to parallax error. Fluid flow rates are uncontrolled during injection and tissue damage may occur due to an "unsteady" injection. Reflux of the drug may also occur when the needle is removed from the eye.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. With this type of dispenser, the volumes delivered are highly dependent on fluid viscosity, surface tension, and the specific dispensing tip. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. While precise, this dispenser is expensive and requires an electrical signal to be delivered to the dispensing mechanism.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a portable hand piece for injecting a drug into the eye. Such a hand piece can include a limited reuse assembly attachable to and removable from a disposable tip segment. The disposable tip segment contains the drug, a needle for administering the drug, and a temperature control device, such as a heater, for altering the temperature of the drug. In order to safely operate such a device, a mechanical lockout feature may be desirable. In addition, for lower cost, spring actuation may also be desirable.

SUMMARY OF THE INVENTION

In one embodiment consistent with the principles of the present invention, the present invention is an ophthalmic injection device including a dispensing chamber housing, a plunger, a needle, a spring, a safety actuator, a lockout bar, and a button. The dispensing chamber housing has an inner surface and an outer surface. The inner surface partially defines a dispensing chamber for receiving a quantity of a substance. The plunger is fluidly sealed to an interior surface of the dispensing chamber housing. The needle is fluidly coupled to the dispensing chamber. The spring provides a force to drive the plunger. The actuator is coupled to the lockout bar. The button interfaces with the lockout bar. The actuator moves the lockout bar when a condition is met, thereby allowing the button to be activated so that the spring provides the force to drive the plunger.

In another embodiment consistent with the principles of the present invention, the present invention is an ophthalmic injection device including a dispensing chamber housing, a plunger, a needle, a temperature control device, a spring, a piston, an actuator, a lockout bar, and a button. The dispensing chamber housing has an inner surface and an outer surface. The inner surface partially defines a dispensing chamber for receiving a quantity of a substance. The plunger is fluidly sealed to an interior surface of the dispensing chamber housing. The needle is fluidly coupled to the dispensing chamber. The temperature control device alters a temperature of the substance. The spring provides a force to drive the plunger. The piston is coupled to the plunger at one end and to the spring at the other end. The actuator is coupled to the lockout bar. The button interfaces with the lockout bar. The actuator moves the lockout bar when the substance reaches a temperature, thereby allowing the button to be activated so that the spring provides the force to drive the plunger.

In another embodiment consistent with the principles of the present invention, the present invention is a method of injecting a substance into an eye, the method comprising: altering the temperature of a substance to be injected into an eye; after the substance reaches a temperature, activating an actuator to move a lockout bar; moving the lockout bar to allow a spring to be activated; and activating the spring to produce a force that pushes a plunger to deliver the substance into the eye.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying figures, which are incorporated in and constitute a part of this specification, illustrate several embodiments of the invention and together with the description, serve to explain the principles of the invention.

FIGS. 4A and 4B are views of a safety linear actuator lockout mechanism according to the principles of the present invention.

FIG. 5 is a side view of a lockout bar according to the principles of the present invention.

DETAILED DESCRIPTION OF THE PREFERRED EMBODIMENTS

Reference is now made in detail to the exemplary embodiments of the invention, examples of which are illustrated in the accompanying figures. Wherever possible, the same reference numbers are used throughout the figures to refer to the same or like parts.

Figure 1:
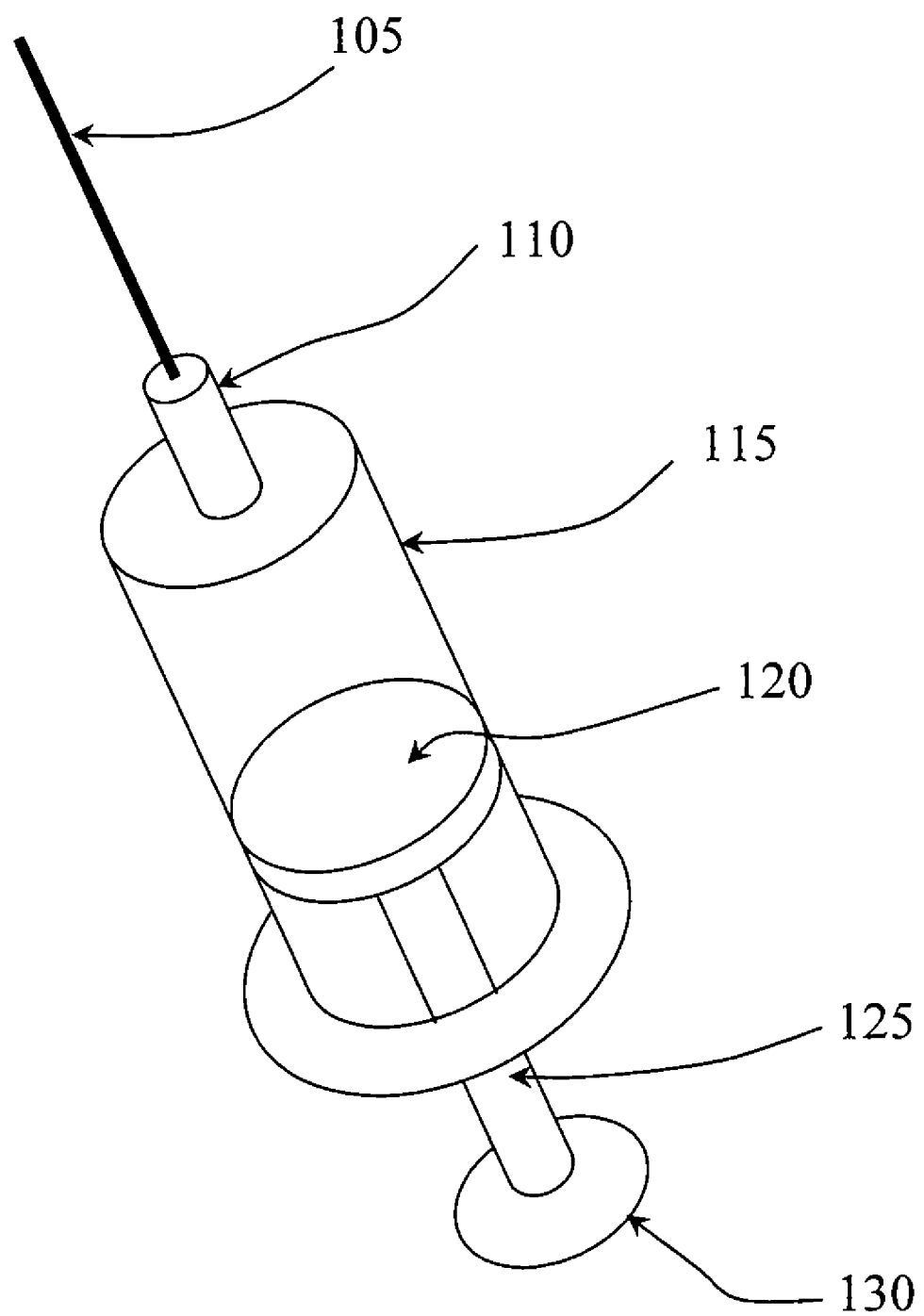
FIG. 1 is a perspective view of a prior art syringe.
Figure 2:
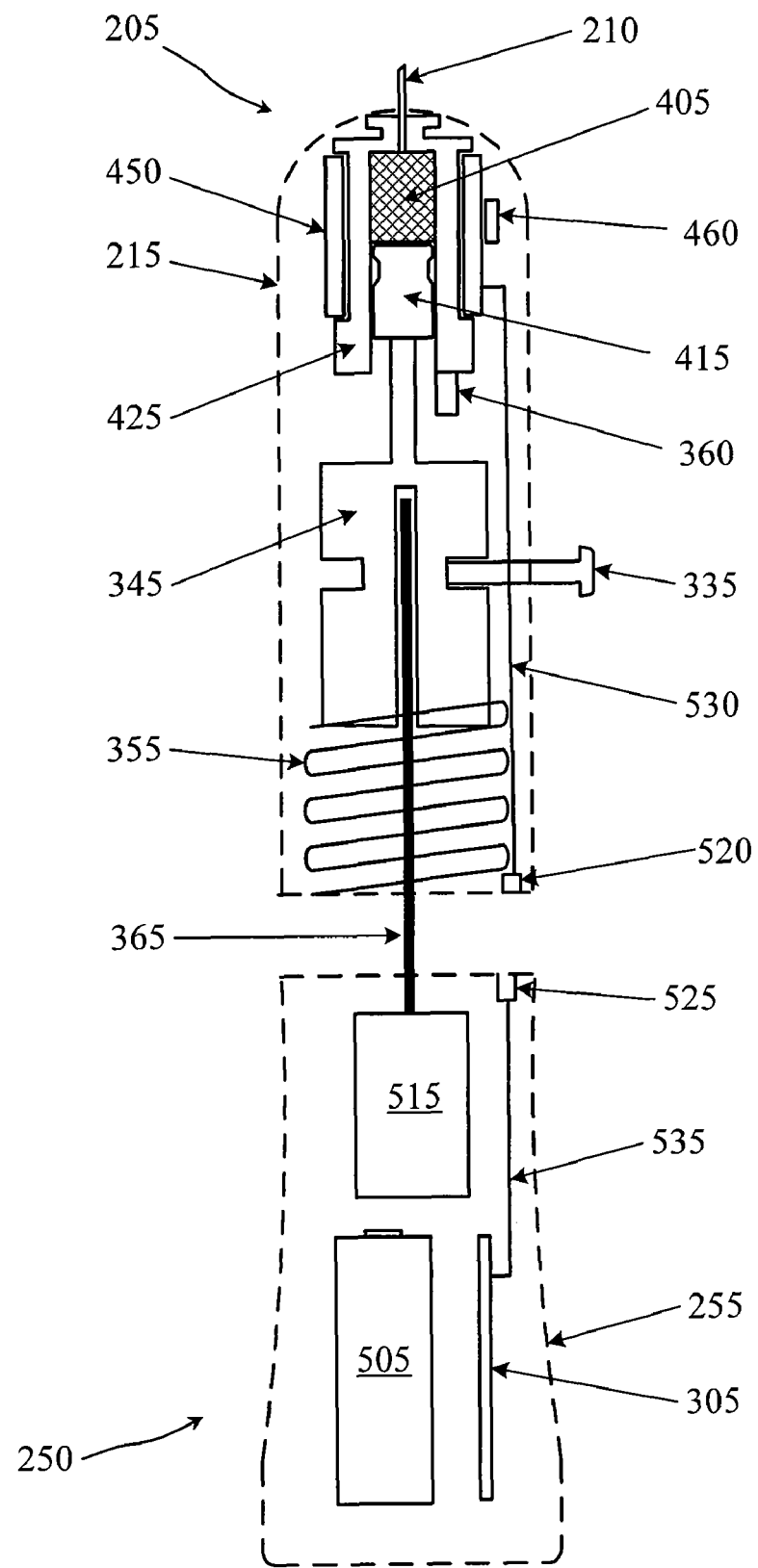
FIG. 2 is a cross section view of an ophthalmic medical device including a disposable tip segment and a limited reuse assembly according to the principles of the present invention.

FIG. 2 is a cross section view of a disposable tip segment and a limited reuse assembly according to an embodiment of the present invention. FIG. 2 shows how tip segment 205 interfaces with limited reuse assembly 250. In the embodiment of FIG. 2, tip segment 205 includes plunger 415, dispensing chamber housing 425, tip segment housing 215, temperature control device 450, thermal sensor 460, needle 210, dispensing chamber 405, button 335, piston 345, spring 355, stop 360, interface 530, and tip interface connector 520. Limited reuse assembly 250 includes safety actuator 515, lockout bar 365, power source 505, controller 305, limited reuse assembly housing 255, interface 535, temperature control device activation button 337, and limited reuse assembly interface connector 525.

In tip segment 205, one end of plunger 415 forms one end of dispensing chamber 405. Plunger 415 is adapted to slide within dispensing chamber 405. An outer surface of plunger 415 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug based on thermal characteristics.

Needle 210 is fluidly coupled to dispensing chamber 405. In such a case, a substance contained in dispensing chamber 405 can pass through needle 210 and into an eye. Temperature control device 450 at least partially surrounds dispensing chamber housing 425. Interface 530 connects temperature control device 450 with tip interface connector 520.

In various embodiments of the present invention, temperature control device 450 is a heating and/or a cooling device. Temperature control device 450 is in thermal contact with dispensing chamber housing 425. As such, temperature control device 450 is capable of changing the temperature of the substance in dispensing chamber 405. Interface 530 and tip interface connector 520 couple temperature control device 450 to a limited reuse assembly. In such a case, temperature control device 450 can be powered and controlled by the limited reuse assembly. Temperature control device activation button 337 can be used to activate temperature control device 450.

A substance to be delivered into an eye, typically a drug, is located in dispensing chamber 405. In this manner, the substance is contacted by the inner surface of dispensing chamber housing 425 and one face of plunger 415. Typically, dispensing chamber 405 is cylindrical in shape. Temperature control device 450 is in thermal contact with dispensing chamber housing 425. In this manner, temperature control device 450 is adapted to control the temperature of the contents of dispensing chamber 425. Thermal sensor 460 provides temperature information to assist in controlling the operation of temperature control device 450.

In one embodiment of the present invention, the substance located in dispensing chamber 405 is a drug that is preloaded into the dispensing chamber. In such a case, disposable tip segment 205 is appropriate as a single use consumable product. Such a disposable product can be assembled at a factory with a dosage of a drug installed.

When a drug is preloaded into dispensing chamber 405, a set quantity of the drug can be preloaded. For example, 100 microliters of a drug can be loaded into dispensing chamber 405, and any quantity up to 100 microliters can be dispensed. In such a case, the plunger 415 can be moved a precise distance to deliver a precise dosage of drug from the dispensing chamber 405, through the needle 210, and into an eye. This provides for flexibility of dosing and for ease of assembly.

Spring 355 is coupled to piston 345, which in turn is coupled to plunger 415. Spring 355 is adapted to drive piston 345 upward when button 335 is activated. In this manner, spring 355 provides the force necessary to move piston 345 and plunger 415 upward to dispense the substance contained in dispensing chamber 405. Spring 355 is selected (generally by selecting its spring constant) to provide a force that drives plunger 415 at a pre-selected rate. For example, if spring 355 has a relatively high spring constant, the rate at which plunger 415 is driven is relatively high—resulting in a fast delivery of the substance in dispensing chamber 405. If spring 355 has a relatively low spring constant, the rate at which plunger 415 is driven is relatively low—resulting in a slow delivery of the substance in dispensing chamber 405.

Button 335 engages lockout bar 365 (as described in further detail below). In this manner, lockout bar 365 traverses piston 345. In this embodiment, lockout bar 365 is inserted into an opening in piston 345. Button 335 also enters piston 335 through an opening that is generally perpendicular to the opening through which lockout bar 365 travels.

A stop 360 is also provided to stop the movement of piston 345 and plunger 415. In this manner, stop 360 can be used as a mechanical dosing device. The location and length of stop 360 determines how far piston 345 and plunger 415 can travel, thus limiting the amount of substance dispensed from dispensing chamber 405.

The components of tip segment 205, including piston 345, spring 355, stop 360, dispensing chamber housing 425, temperature control device 450, and plunger 415 are at least partially enclosed by tip segment housing 215. In one embodiment consistent with the principles of the present invention, plunger 415 is sealed to the interior surface of dispensing chamber housing 425. This seal prevents contamination of any substance contained in dispensing chamber 405. For medical purposes, such a seal is desirable. This seal can be located at any point on plunger 415 or dispensing chamber housing 425.

In limited reuse assembly 250, power source 505 provides power to safety actuator 515. An interface (not shown) between power source 505 and safety actuator 515 serves as a conduit for providing power to safety actuator 515. Safety actuator 515 is connected to lockout bar 365.

Controller 305 is connected via interface 535 to limited reuse assembly interface connector 525. Limited reuse assembly interface connector 525 is located on a top surface of limited reuse assembly housing 255. In this manner, limited reuse assembly interface connector 525 is adapted to be connected with tip interface connector 520.

Controller 305 and safety actuator 515 are connected by an interface (not shown). This interface (not shown) allows controller 305 to control the operation of safety actuator 515. In addition, an interface (not shown) between power source 505 and controller 305 allows controller 305 to control operation of power source of 505. In such a case, controller 305 may control the charging and the discharging of power source 505 when power source 505 is a rechargeable battery.

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control a temperature control device. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component, controller 305 may be made of many different components or integrated circuits.

Safety actuator 515 is typically a linear actuator or linear driver. In such a case, safety actuator 515 may be a spring or spring driven mechanism, a geared DC motor with a rotary sensor coupled to a linear drive or a dc motor coupled to a linear drive with a linear sensor, or a linear stepper motor. Other types of motors, like a rotational permanent magnet motor, may also be used for safety actuator 515.

Tip segment 205 is adapted to mate with or attach to limited reuse assembly 250 as previously described. In the embodiment of FIG. 2, tip interface connector 520 is adapted to connect with limited reuse assembly interface connector 525. In addition, an interface is formed between controller 305 and temperature control device 450. A signal can pass from controller 305 to temperature control device 450 through interface 535, limited reuse assembly interface connector 525, tip interface connector 520, and interface 530.

In addition, controller 305 controls the operation of temperature control device 450. Temperature control device 450 is adapted to heat and/or cool dispensing chamber housing 425. Since dispensing chamber housing 425 is at least partially thermally conductive, heating or cooling dispensing chamber housing 425 heats or cools a substance located in dispensing chamber 405. Temperature information can be transferred from thermal sensor 460 to controller 305 via any of a number of different interface configurations. This temperature information can be used to control the operation of temperature control device 450. When temperature control device 450 is a heater, controller 305 controls the amount of current that is sent to temperature control device 450. The more current sent to temperature control device 450, the hotter it gets. In such a manner, controller 305 can use a feed back loop utilizing information from thermal sensor 460 to control the operation of temperature control device 450. Any suitable type of control algorithm, such as a proportional integral derivative (PID) algorithm, can be used to control the operation of temperature control device 450.

In operation, when tip segment 205 is connected to limited reuse assembly 250, controller 305 controls the operation of temperature control device 450 and safety actuator 515. First, the substance in dispensing chamber 405 is heated or cooled (as the case may be). When the substance reaches the proper temperature, controller activates safety actuator 515. Safety actuator 515 moves lockout bar 365 to a position that allows button 335 to be depressed. Depressing button 335 allows spring 355 to drive piston 345 and plunger 415, thus dispensing the substance contained in dispensing chamber 405. In this manner, safety actuator 515 only allows an injection to take place when the substance is in the proper temperature range. An upper and/or lower temperature limit (or both—i.e. a range) can be provided to control safety actuator 515. Safety actuator 515 moves the lockout bar 365 when the temperature condition is met. In other embodiments of the present invention, other conditions may be met before safety actuator 515 moves lockout bar 365. For example, various safety conditions (tip segment properly attached to limited reuse assembly, properly functioning mechanics or electronics, proper dosage selection, etc.) may be met before safety actuator 515 moves lockout bar 365.

While depicted as being a part of tip segment 205, piston 345, spring 355, lockout bar 365, and button 335 or any combination of them may be found in limited reuse assembly 250. For example, in one embodiment consistent with the principles of the present invention, piston 345, spring 355, lockout bar 365, and button 335 are all a part of limited reuse assembly 250. In this configuration, piston 345 interfaces with plunger 415 or a shaft attached to the bottom of plunger 415. In this manner, tip segment contains fewer parts than depicted in FIG. 2 resulting in fewer parts that are discarded after an injection.

Figure 3:
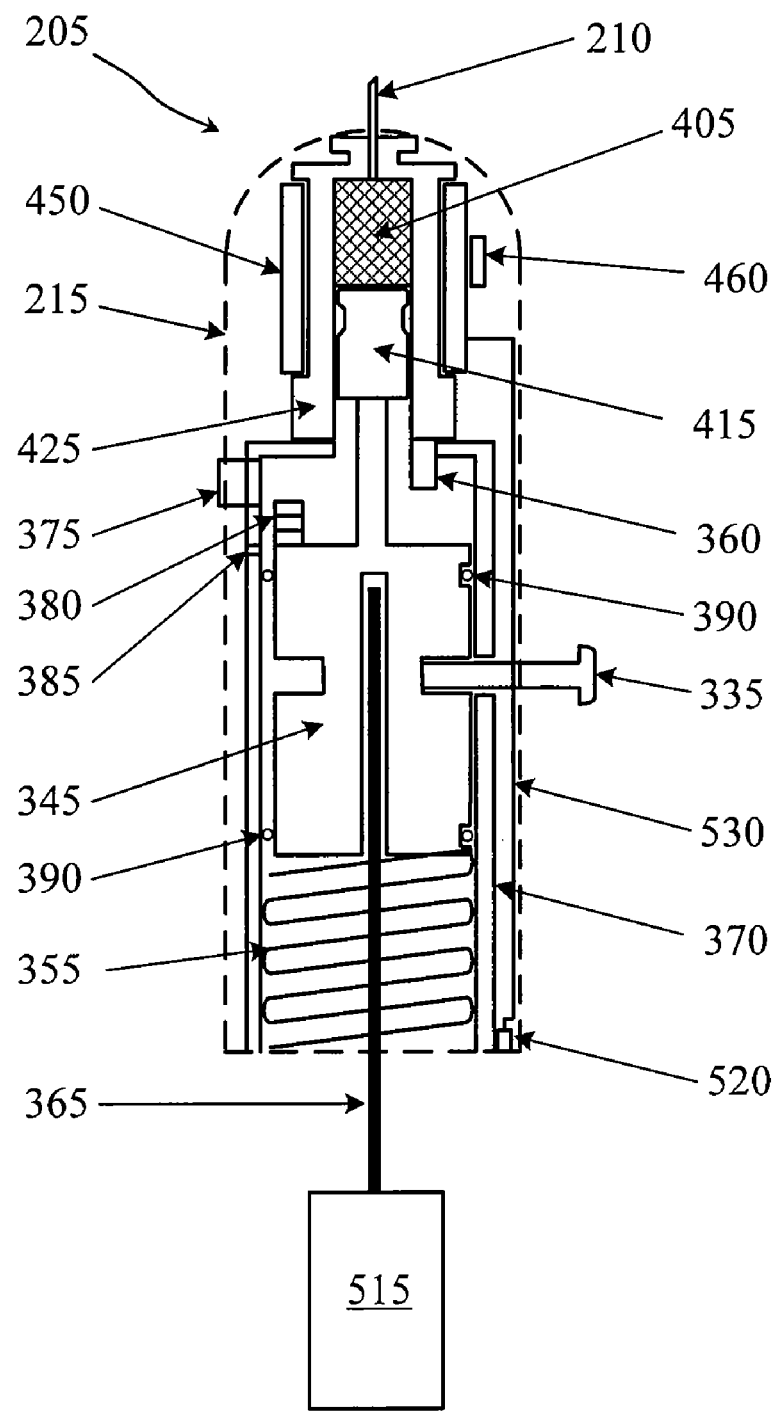
FIG. 3 is a cross section view of an embodiment of a disposable tip segment and safety linear actuator lockout mechanism according to the principles of the present invention.

FIG. 3 is a cross section view of an embodiment of a disposable tip segment and safety linear actuator lockout mechanism according to the principles of the present invention. The tip segment 205 of FIG. 3 includes a few additional features not pictured in FIG. 2. These new features include an internal housing 370, window 375, indicator 380, vent 385, and one or more o-rings 390. The remaining components of tip segment 205 are described with reference to FIG. 2.

Internal housing 370 at least partially encloses piston 345. In this manner, internal housing 370 provides a space in which piston 345 travels. Typically, this space is generally cylindrical, as is piston 345. A window 375 is included in tip segment housing 215 to allow indicator 380 to be seen. Indicator 380 is a mechanical indicator that moves with piston 345. In this manner, as piston 345 moves (moving plunger 415 and dispensing the substance from dispensing chamber 405), indicator 380 also moves. Indicator 380 has colors, numbers, or the like that are designed to visually confirm the success or failure of an injection. For example, if piston 345 moves properly (and is stopped by stop 360), then indicator 380 moves upward so that an indication of a successful injection is displayed through window 375.

Vent 385 is located in internal housing 370. One or more o-rings 390 provide a seal between piston 345 and the interior of internal housing 370. Both vent 385 and o-rings 390 are optional. Vent 385 is provided to allow air to escape from the interior of internal housing 370. This allows piston 345 to move upward. When one or more o-rings 390 are used (or another suitable seal is formed between piston 345 and the interior surface of internal housing 370), the size of vent 385 can determine how fast piston 345 is allowed to move. For a given force provided by spring 355, the size of vent 385 acts to damp the movement of piston 345 (which movement is constrained by the rate at which the air entrapped in internal housing 370 escapes through vent 385). In this manner, a controlled movement of piston 345 can be achieved.

FIGS. 4A and 4B are views of a safety linear actuator lockout mechanism according to the principles of the present invention. FIGS. 4A and 4B show the movement of lockout bar 365 and the position of button 335 with respect to lockout bar 365. Safety actuator moves lockout bar 365 downward revealing an opening through which one end of button 335 passes. This opening is shown in FIG. 5. FIG. 5 is a side view of a lockout bar according to the principles of the present invention.

Figure 6A:
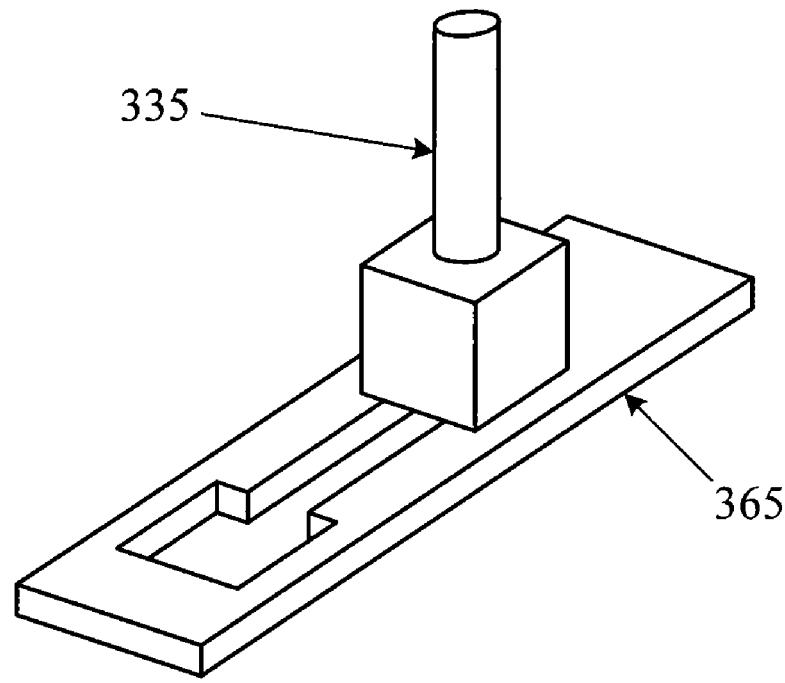
FIGS. 6A and 6B are perspective views of a lockout mechanism according to the principles of the present invention.
Figure 6B:
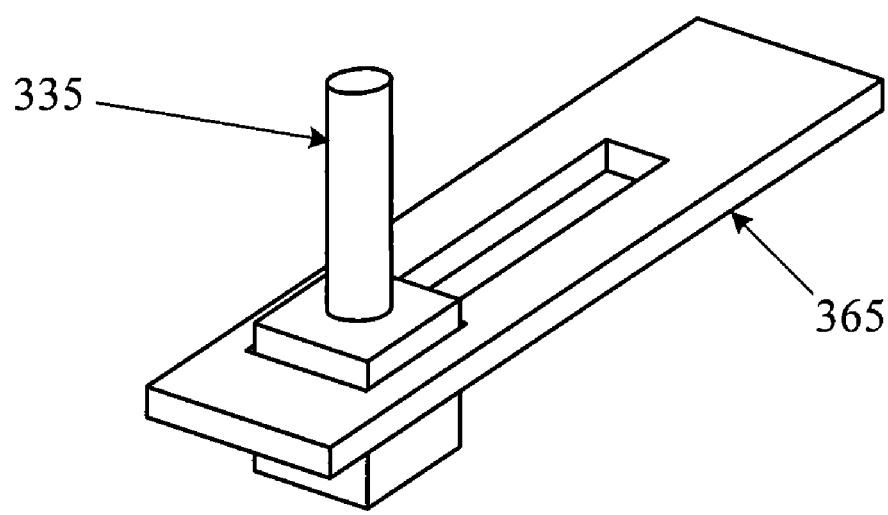

FIGS. 6 and 6B are perspective views of a lockout mechanism according to the principles of the present invention. FIGS. 6A and 6B show the shapes and relative movement of button 335 and lockout bar 365. As shown, one end of button 335 is shaped and/or sized to fit through an opening in lockout bar 365. Safety actuator 515 is coupled to lockout bar 365. After a certain condition is met (such as the substance reaching the proper temperature), safety actuator 515 moves lockout bar 365 so that one end of button 335 can pass through lockout bar 365. When button 335 passes through lockout bar 365, piston 345 is allowed to move. Spring 355 drives piston 345 and plunger 415 to dispense the substance contained in dispensing chamber 405.

From the above, it may be appreciated that the present invention provides an improved system for delivering precise volumes of a substance into an eye. The present invention provides a single use, disposable delivery device tip segment that is capable of delivering a precise dosage. The tip segment interfaces with a limited reuse assembly. A safety actuator prevents the substance from being dispensed until a certain condition is met. When the condition is met, the safety actuator moves a lockout bar that allows the injection to take place. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic injection device comprising:
a dispensing chamber housing having an inner surface and an outer surface, the inner surface partially defining a dispensing chamber for receiving a quantity of a substance;
a plunger fluidly sealed to an interior surface of the dispensing chamber housing;
a needle fluidly coupled to the dispensing chamber;
a spring for providing a force to drive the plunger;
an actuator coupled to a lockout bar, the lockout bar having an opening with a first shape; and
a button that interfaces with the lockout bar, the button having an end with a second shape that is configured to fit in the opening;
wherein the actuator moves the lockout bar when a condition is met, thereby allowing the button to be activated which allows the spring to provide the force to drive the plunger.

2. The device of claim 1 further comprising:
a temperature control device for altering a temperature of the substance.

3. The device of claim 2 further comprising:
a thermal sensor located near the dispensing chamber housing.

4. The device of claim 1 further comprising:
a piston coupled to the plunger at one end and to the spring at the other end.

5. The device of claim 1 further comprising:
a controller for controlling the actuator.

6. The device of claim 1 wherein the button is activated when the end with the second shape fits into the opening.

7. The device of claim 1 wherein the lockout bar is moved when the substance reaches a temperature.

8. The device of claim 4 further comprising:
an internal housing at least partially surrounding the piston; and
an external housing at least partially surrounding the dispensing chamber housing and the internal housing.

9. The device of claim 8 further comprising:
a seal between an exterior surface of the piston and an interior surface of the internal housing.

10. The device of claim 9 further comprising:
a vent located in a wall of the internal housing, the vent for allowing air to escape from the interior of the internal housing.

11. The device of claim 10 wherein the force produced by the spring moves the piston and air in the internal housing is pushed through the vent by the piston thus acting as a damper.

12. The device of claim 1 further comprising:
a stop designed to interface with a piston such that the plunger moves a distance determined by the length of the stop.

13. An ophthalmic injection device comprising:
a dispensing chamber housing having an inner surface and an outer surface, the inner surface partially defining a dispensing chamber for receiving a quantity of a substance;
a plunger fluidly sealed to an interior surface of the dispensing chamber housing;
a needle fluidly coupled to the dispensing chamber;
a spring for providing a force to drive the plunger;
a piston coupled to the plunger at one end and to the spring at the other end;
an internal housing at least partially surrounding the piston;
an external housing at least partially surrounding the dispensing chamber housing and the internal housing;
a seal between an exterior surface of the piston and an interior surface of the internal housing;
a vent located in a wall of the internal housing, the vent for allowing air to escape from the interior of the internal housing;
an actuator coupled to a lockout bar; and
a button that interfaces with the lockout bar;
wherein the actuator moves the lockout bar when a condition is met, thereby allowing the button to be activated which allows the spring to provide the force to drive the plunger.

14. The device of claim 13 further comprising:

a temperature control device for altering a temperature of the substance.

15. The device of claim 14 further comprising:

a thermal sensor located near the dispensing chamber housing.

16. The device of claim 13 further comprising:

a controller for controlling the actuator.

17. The device of claim 13 wherein the lockout bar has an opening with a first shape and the button has an end with a second shape that is configured to fit in the opening.

18. The device of claim 17 wherein the button is activated when the end with the second shape fits into the opening.

19. The device of claim 13 wherein the lockout bar is moved when the substance reaches a temperature.

20. The device of claim 13 wherein the force produced by the spring moves the piston and air in the internal housing is pushed through the vent by the piston thus acting as a damper.

21. The device of claim 13 further comprising:

a stop designed to interface with a piston such that the plunger moves a distance determined by the length of the stop.

* * * * *